(12) United States Patent
Murtagh et al.

(10) Patent No.: US 7,659,979 B2
(45) Date of Patent: Feb. 9, 2010

(54) OPTICAL INSPECTION APPARATUS AND METHOD

(75) Inventors: Martin Edward Murtagh, Carrigaline (IE); Patrick Vincent Kelly, Galway (IE); Houssam Chouaib, Lyons (FR); Vincent Guénebaut, Cork (IE)

(73) Assignee: KLA-Tencor Corporation, Milpitas, CA (US)

( * ) Notice: Subject to any disclaimer, the term of this patent is extended or adjusted under 35 U.S.C. 154(b) by 109 days.

(21) Appl. No.: 11/869,969

(22) Filed: Oct. 10, 2007

(65) Prior Publication Data

US 2008/0218741 A1 Sep. 11, 2008

Related U.S. Application Data

(60) Provisional application No. 60/852,007, filed on Oct. 17, 2006.

(51) Int. Cl.
*G01N 21/00* (2006.01)
*G01J 3/28* (2006.01)

(52) U.S. Cl. .................... 356/326; 356/237.2; 356/432; 356/442

(58) Field of Classification Search .... 356/237.1–243.8
See application file for complete search history.

(56) References Cited

U.S. PATENT DOCUMENTS

| 5,243,983 | A * | 9/1993 | Tarr et al. ................. 600/318 |
| 5,255,071 | A * | 10/1993 | Pollak et al. ............... 356/417 |
| 6,271,921 | B1 * | 8/2001 | Maris et al. ................ 356/432 |
| 6,865,014 | B2 * | 3/2005 | Ciesla et al. ............... 359/326 |
| 7,016,044 | B2 * | 3/2006 | Murtagh et al. ............ 356/432 |
| 7,420,684 | B2 * | 9/2008 | Takeuchi et al. ............ 356/445 |

* cited by examiner

*Primary Examiner*—Gregory J Toatley, Jr.
*Assistant Examiner*—Jarreas C Underwood
(74) *Attorney, Agent, or Firm*—Luedeka, Neely & Graham, P.C.

(57) ABSTRACT

Performing modulation spectroscopy by directing a probe beam and a pump beam at a strained semiconductor sample, modulating the pump beam, and reflecting the probe beam into a detector. The detector produces a direct current signal proportional to reflectance R of the probe beam and an alternating current signal proportional to the modulation of the reflectance ΔR of the probe beam. Both R and ΔR are measured at a multiplicity of probe beam photon energies, to provide a spectrum having at least one line shape. The spectrum is analyzed to measure energy differences between interband electronic transitions of the sample, and the strain of the sample is determined from the energy differences.

5 Claims, 7 Drawing Sheets

Computer control (36):
- for selection of appropriate mode of modulation optical arrangement/illumination
- for selection of appropriate mode of electronics modules
- for positioning sample
- for data acquisition/analysis Computer control (36):
- for selection of appropriate mode of modulation optical arrangement/illumination
- for selection of appropriate mode of electronics modules
- for positioning sample
- for data acquisition/analysis

Fig. 4

Signals ΔR detected by the lock-in amplifier (35) and R detected by the analogue-to-digital converter of meter (34) as a function of time. Note that the ΔR is typically several orders of magnitude smaller than the R signal; the graph of ΔR is shown on an expanded scale for clarity. The lower panel shows the typical behaviour of the modulated reflectance signal ratio ΔR/R with spectral position (expressed in Photon Energy) in the region of the direct bandgap energy ($E_g$) of a semiconductor.

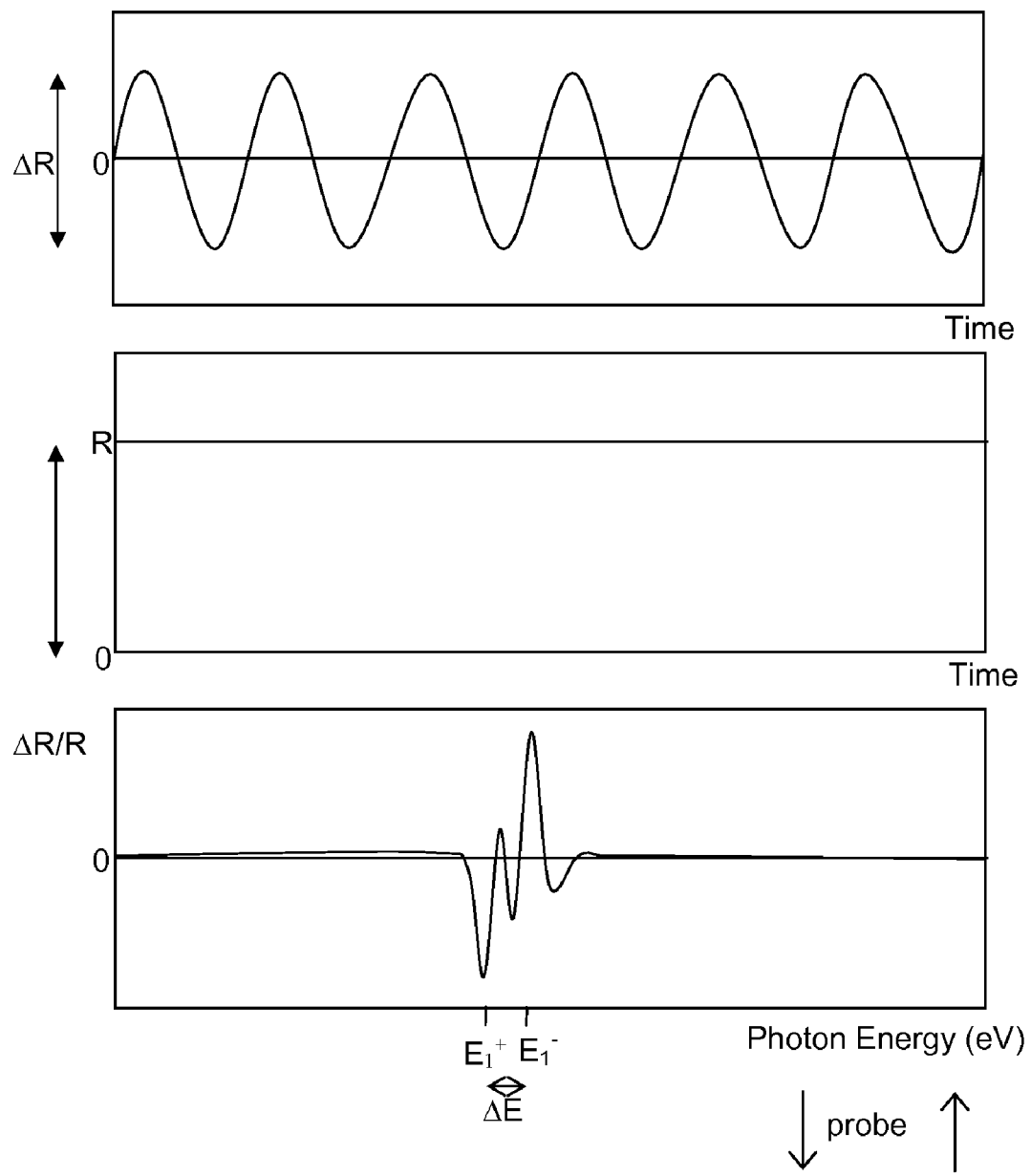

US 7,659,979 B2

OPTICAL INSPECTION APPARATUS AND METHOD

RELATED APPLICATIONS

This application claims the benefit of U.S. Provisional Application No. 60/852,007, filed Oct. 17, 2006.

BACKGROUND

Technologically useful forms of strained silicon are those in which the silicon is strained by pseudomorphic growth as an ultra-thin layer of silicon on a silicon-germanium alloy buffer layer, or in which the strained silicon thus grown has been transferred as a thin layer onto an insulating layer on a second wafer so-called strained silicon on insulator, or else where the strain is induced by means of adjacent regions of silicon-germanium alloy.

These forms of strained silicon present difficulties to X-ray diffractometry or Raman spectroscopy when applied to them to measure the strain in the silicon layer. X-rays are not easily absorbed in silicon or in silicon-germanium alloy or insulators. Therefore, the depth from which information is generated in an X-ray diffractometry measurement is much larger than the technologically useful thickness of a strained silicon layer, typically 20 nm. When X-ray diffractometry is performed, for example, on a pseudomorphically grown ultra-thin layer of silicon on a silicon-germanium alloy buffer layer, almost all of the signal is generated from the underlying silicon-germanium alloy, and the crystallographic information determined is from this layer, even at grazing incidence of the x-ray and when measuring for long times. In extreme cases of measurement time and grazing incidence, information specific to the top strained silicon layer can be gleaned from an X-ray diffractometry measurement, but the time taken renders the measurement impractical for the examination of large numbers of samples in a short time. More generally, what is done is to measure the lattice constant of the underlying silicon-germanium alloy and calculate the strain in the top layer. This again is time-consuming, fails to measure the actual strain in the silicon itself, and is impossible in silicon-on-insulator structures.

The invention is directed towards achieving improved inspection of strained silicon or like materials.

SUMMARY

According to embodiments of the invention, there is provided a method for modulation spectroscopy inspection of a semiconductor sample, the method comprising the steps of: directing an incident probe beam at the sample and detecting a reflected probe beam at a detector; modulating a pump beam, and directing the modulated pump beam at the sample to cause modulation of reflectance of the probe beam so that the detector generates as output a d.c. signal proportional to reflectance R of the probe beam and an a.c. modulated signal proportional to the modulation of the reflectance $\Delta R$ of the probe beam; and irradiating the sample in a manner to increase the ratio $\Delta R:R$ In one embodiment, the sample is irradiated by the generating probe beam with properties to cause the increase in the $\Delta R:R$ ratio.

In one embodiment, the sample is irradiated by a source other than the probe beam.

In one embodiment, the source is dedicated to achieving an increase in the $\Delta R:R$ ratio.

In one embodiment, the sample is irradiated prior to detection of R and $\Delta R$, to condition the sample.

In one embodiment, the sample is irradiated to photo-induce changes in the sample.

In one embodiment, the changes are transient.

In another embodiment, the changes are permanent.

In one embodiment, the sample is irradiated to photo-induce changes in electrical, electronic, or optical characteristics of the sample.

In one embodiment, the sample is irradiated with UV radiation.

In another embodiment, the sample is irradiated with IR radiation.

In one embodiment, the sample is irradiated with visible radiation.

In one embodiment, the sample is irradiated by a combination of UV, IR, and visible radiation.

In one embodiment, the sample is a strained semiconductor sample.

In another aspect, the invention provides an analysis system comprising means for performing any method as defined above.

BRIEF DESCRIPTION OF THE DRAWINGS

The invention will be more clearly understood from the following description of some embodiments thereof, given by way of example only with reference to the accompanying drawings in which:—

FIG. 4 shows plots of reflectance and modulated reflectance signals with time;

DETAILED DESCRIPTION

Figure 1:
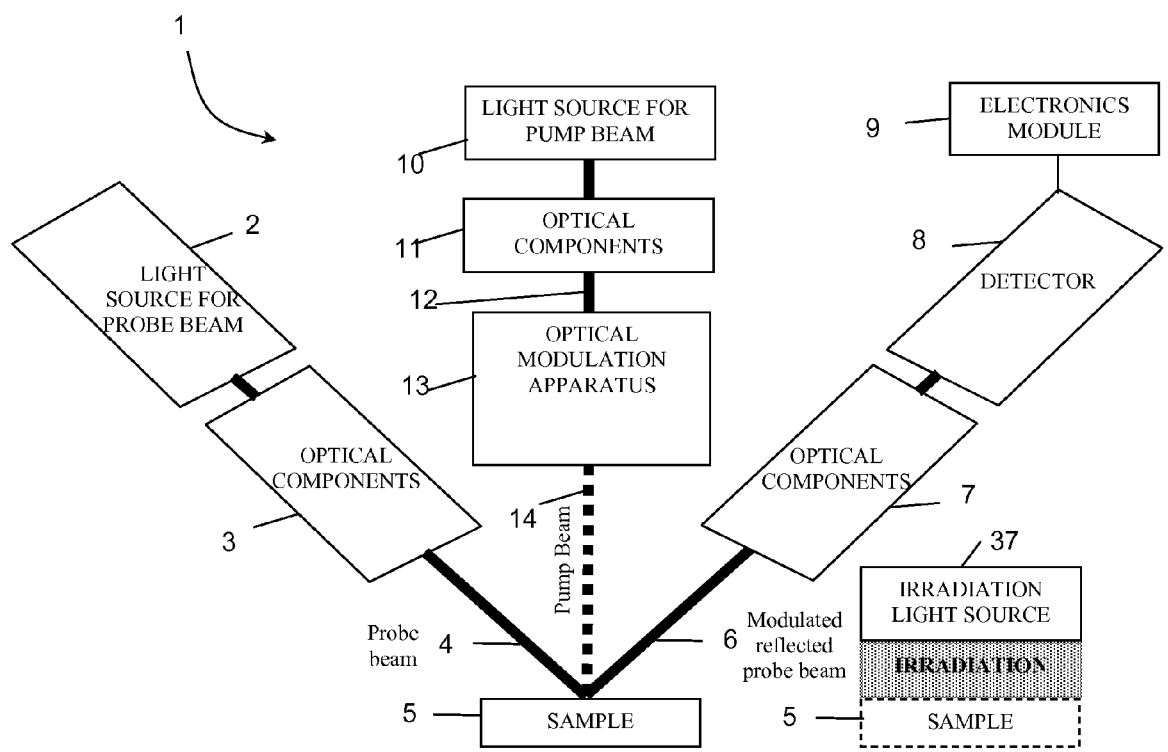
FIG. 1 is a diagrammatic overview.
Figure 2:
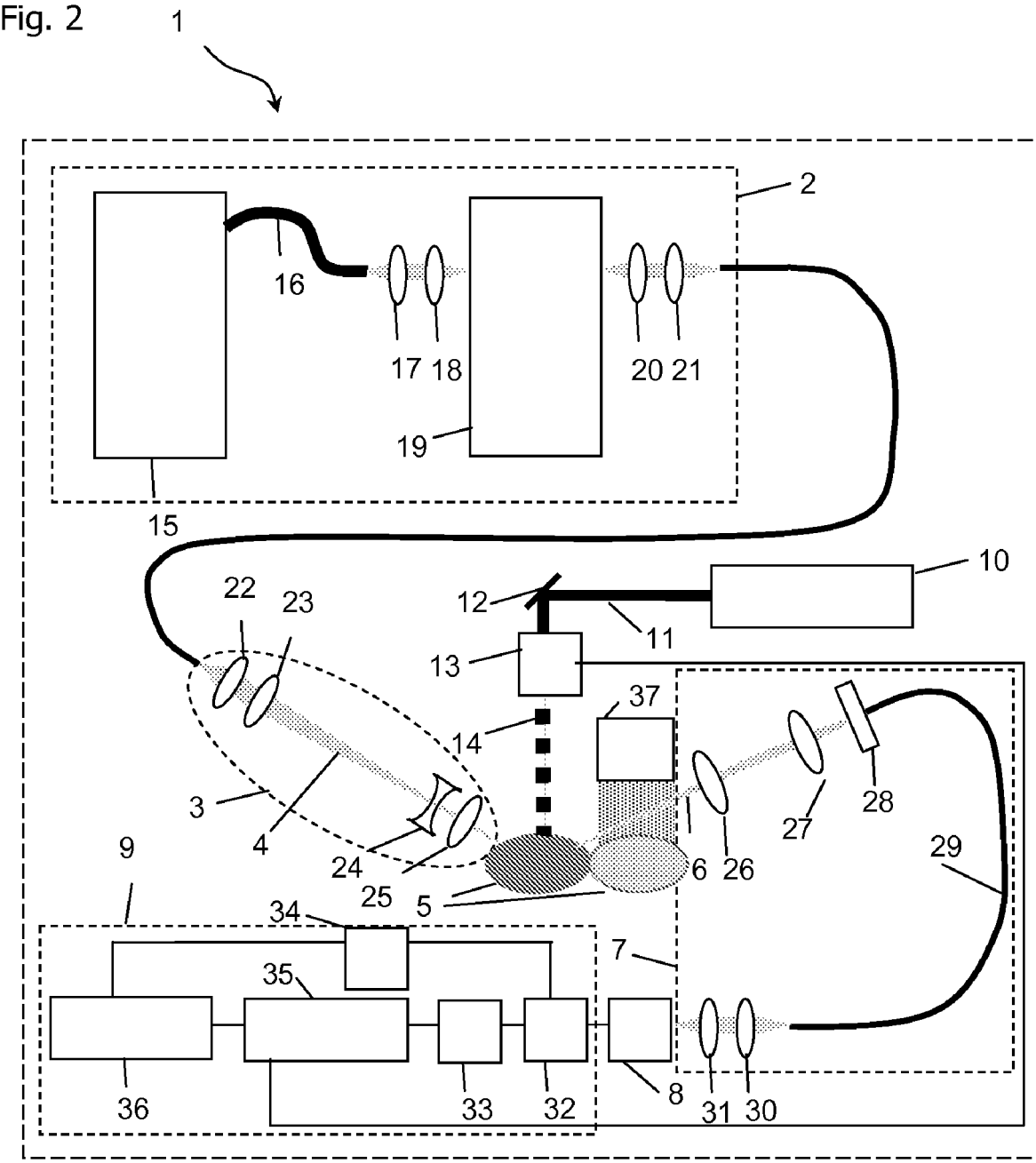
FIG. 2 is a more detailed view of an inspection system of the invention with monochromation of a probe beam prior to its incidence on a sample.

Referring to FIGS. 1 and 2 in an inspection apparatus 1 a probe beam light source 2 generates an incident probe beam 4 on a strained silicon sample 5. A modulated reflected probe beam 6 is detected by a probe beam detector 8. Also, a pump beam 12 is modulated by a modulator 13 and the modulated pump beam is indicated by the numeral 14. The sample 5 may be moved to a second position called the irradiation position, shown in FIG. 1. enclosed in dotted lines on the right of the sample measurement position, and may be irradiated by an external light source 37 which may comprise an optical fibre, and which may irradiate some or all of the sample area. In some embodiments of the invention, the irradiation may be performed in the measurement position, using either an external light source 37 or by using the probe beam or the pump beam prior to measurement.

Within the probe beam light source 2 (or in another embodiment, within the optical components 7) a monochromator or spectrograph 19 spatially disperses the light into its constituent wavelengths such that the photoreflectance signal can be measured at a multiplicity of wavelengths. A typical form of the result of the modulation spectroscopy measurement is shown in FIG. 4, which is a spectrum of the ratio of the modulated reflectance signal □R to the reflectance signal R, in this case typical of the result from a thin 20 nm strained silicon layer pseudomorphically grown on a fully relaxed silicon-germanium alloy layer of Ge alloy mole fraction 20%.

The system 1 measures the direct interband transition energies (sometimes referred to as the optical bandgaps) of semiconductors using the method of modulation spectroscopy known also as photoreflectance spectroscopy. It may be used to determine strain and/or alloy composition in silicon, germanium, silicon-germanium alloy, silicon-germanium-carbon alloy, silicon-on-insulator, silicon-germanium-on-insulator or other semiconductor materials and semiconductor structures.

The apparatus 1 may comprises a mechanical support system of the type described in WO2005/015187.

The light source sub-system 2 comprises a light source 15 coupled by means of a fibre optic 16 and a pair of lenses 17 and 18, one of which 17 has a suitable f-number compared to the f-number of the fibre optic or fibre optic bundle 16 and the other of which has a suitable f-number compared to the f-number of a monochromator 19. They cause the light from the lens 18 to fill most of the width of the grating or other dispersive optical element contained within the monochromator 19 in order to obtain a near-optimum spectral resolution from the monochromator 19. This produces a monochromated light beam which is coupled by means of a pair of lenses of suitable f-number into a fibre optic forming part of an input optical probe beam subsystem 3.

The input optical probe beam subsystem 3 comprises a pair of lenses 22 and 23, the second of which is the objective lens of a Galilean telescope, the eyepiece lens 2 of which is placed such that a parallel probe beam 4 of de-magnified diameter is produced at the output of the lens 24, and is focused using a high-f-number lens 25 onto a sample material 5.

The pump optical source 10 is coupled by a mirror 12 to a modulation system 13, which modulates the pump beam 11 into a modulated pump beam 14 directed to an area of coincidence with the area of incidence of the probe beam 4 on the sample 5.

The output optical probe beam subsystem 7 comprises lenses 26 and 27 coupling the beam through a filter 28 into a fibre optic 29, the output of which is coupled through a pair of lenses 30 and 31 of suitable f-number onto a silicon photodiode detector 8. The filter 28 is a notch filter (or alternatively a long-pass filter) having negligible transmission at the wavelength of the pump light source 10 but high transmission at least over a wide spectrum of wavelengths longer than the wavelength of the pump light source 10 and extending over the wavelengths at which the modulated reflectance of the sample 5 is to be measured.

The electrical signal produced by the detector 8 is coupled through a transimpedance stage device 32, and also through electrical amplifier devices 33, to a lock-in amplifier 35 which uses a reference frequency signal derived from the same source as that driving the modulator 6. The signals read by the lock-in amplifier are read by the controlling computer 36, which controls several of the other modules of the system including an analogue-to-digital converter or other meter 34 for measuring the d.c. reflectance signal.

Figure 3:
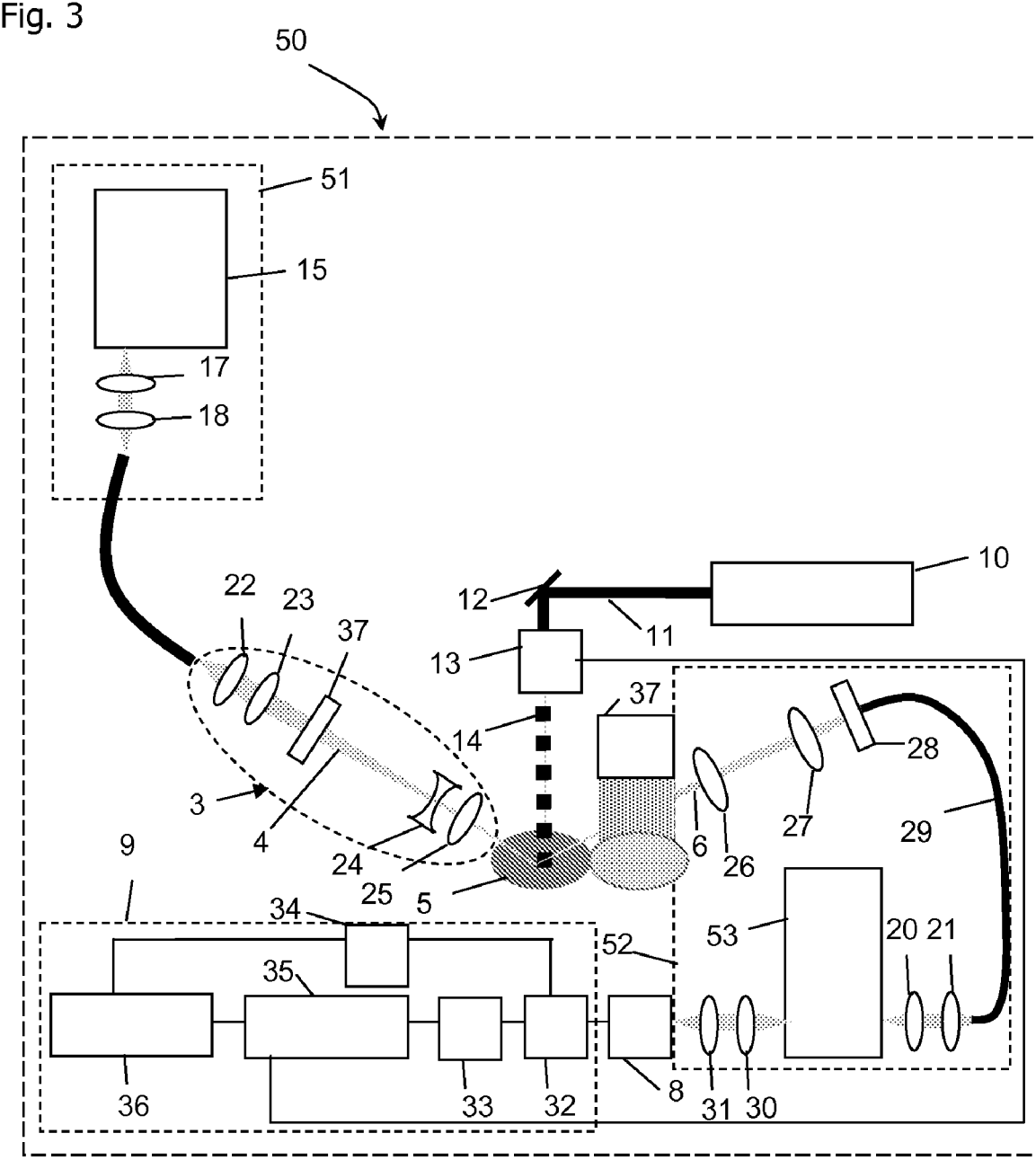
FIG. 3 is a diagrammatic view of a system in which there is monochromation of the probe beam after its reflection from the sample.

In another embodiment the probe beam is monochromated after its reflection from the sample, and such an inspection apparatus, 50, is illustrated in FIG. 3. The apparatus 50 comprises the following, in which like parts are accorded the same reference numerals.

A probe beam light source subsystem 51 comprising a light source 15 coupled by lenses 17 and 18 of suitable f-number into a fibre optic.

The input optical probe beam subsystem 3.

The pump optical source 10, coupled as described above with reference to FIG. 2

An output optical probe beam subsystem 52 comprising lenses 26, 27, a filter 28 and a fibre optic 29 as described above with reference to FIG. 2. The output of the fibre 29 is coupled through a pair of lenses 20, 21, one of which 21 has a suitable f-number compared to the f-number of a monochromator 53 such that it causes the light from lens 21 to fill most of the width of a grating contained within the monochromator 53 in order to obtain a near-optimum spectral resolution from the monochromator 53. The filter 28 is a notch filter having negligible transmission at the wavelength of the pump light source 10 but high transmission at least over a wide spectrum of wavelengths longer than the wavelength of the pump light source 10 and extending over the wavelengths at which the modulated reflectance of the sample 5 is to be measured.

The sample 5 may be moved to a second position called the irradiation position, shown in FIGS. 2 and 3. as a lighter grey wafer on the right of the sample measurement position, and may be irradiated by an external light source 37 which may comprise an optical fibre, and which may irradiate some or all of the sample area. In some embodiments of the invention, the irradiation may be performed in the measurement position, using either an external light source 37 or by using the probe beam or the pump beam prior to measurement.

The signals read by the lock-in amplifier 35 are read by the controlling computer 36.

The measurement method comprises the steps of irradiating the sample, or part thereof, and then, within a suitable time period thereafter, during which the irradiation of the sample by any external irradiation source (other than the probe beam or pump beam) may be discontinued, making a measurement of the photoreflectance spectrum of the sample being the dimensionless quantity □R/R as a function of wavelength over a suitable wavelength range including at least the wavelengths in the region of one strain-dependent interband electronic transition energy. The photoreflectance spectrum is then fitted to a theoretical formalism describing the lineshapes within the spectrum, and which is dependent on the transition energy of the strain-dependent transition, and the strain in the semiconductor can be determined from the value of this strain-dependent transition energy determined from the fitting process.

The photoreflectance spectrum, even if recorded in the absence of the prior irradiation step, will have a certain peak-to-peak magnitude between the highest value and the lowest value of ΔR/R expressed in dimensionless terms, within the range of the spectrum which includes the part of the photoreflectance response of the strained semiconductor which is strain-dependent in its transition energy. The purpose of the prior irradiation step is to photo-induce at least one effect which results in the increase of the peak-to-peak magnitude between the highest value and the lowest value of ΔR/R expressed in dimensionless terms, within the range of the spectrum which includes the part of the photoreflectance response of the strained semiconductor which is strain-dependent in its transition energy. The effect by which this increase is photo-induced appears to arise from one of several effects, including, but not limited to the following:

(i) Photo-induced production of charge carriers in the strained semiconductor or in other layers of the semiconductor structure which may include insulating layers.

(ii) Photo-induced filling of trap or other states of relatively long lifetime in the strained semiconductor or in other layers of the semiconductor structure which may include insulating layers.

(iii) Photo-induced discharging of trap or other states of relatively long lifetime in the strained semiconductor or in other layers of the semiconductor structure which may include insulating layers.

(iv) Photo-induced modification of the electric field strength at the surface or at one or more interfaces within the strained semiconductor or in other layers of the semiconductor structure which may include insulating layers.

(v) Photo-induced reduction of the broadening parameter $\Delta$ which is referred to in equation (1) below, the effect of which, for a photoreflectance lineshape of a given amplitude A, transition energy Eg and phase $\theta$, would be to increase the peak-to-peak value of $\Delta$ R/R expressed in dimensionless terms. The photo-induced reduction of the broadening parameter may be due to one or more other photo-induced effects in the strained semiconductor or in other layers of the semiconductor structure which may include insulating layers.

The photo-induced increase in the peak-to-peak value of $\Delta$ R/R may require a finite time, called the irradiation time, before the increase in the peak-to-peak value of $\Delta$ R/R reaches close to its ultimate value on constant irradiation. The irradiation time may be chosen such that it is sufficiently short to be useful for measurements without an inordinate delay, while being sufficiently long to produce most of the ultimate increase in the peak-to-peak value of $\Delta$ R/R.

The photo-induced increase in the peak-to-peak value of $\Delta$ R/R may gradually reduce again, over a finite time, called the dark time, after the irradiation by an external source is stopped. The reduction in the photo-induced increase in the peak-to-peak value of $\Delta$ R/R may be negligible for practical purposes for a sufficient period of time to allow a multiplicity of photoreflectance spectrum measurements to be made on the sample, over a period of time called the enhanced measurement time.

This effect, which has been observed by the inventors for measurements on samples of strained silicon on insulator, is of particular practical importance and utility. The performance of the photoreflectance spectrum measurements, using a pump beam and a probe beam either or both of which comprise sufficient intensity of irradiation at wavelengths which photo-induce the increase in the peak-to-peak value of $\Delta$ R/R, may increase the duration of the enhanced measurement time. In some methods of the invention, the performance of the photoreflectance spectrum measurements, using a pump beam and a probe beam either or both of which comprise sufficient intensity of irradiation at wavelengths which photo-induce the increase in the peak-to-peak value of $\Delta$ R/R, may be sufficient in itself to sufficiently produce the increase in the peak-to-peak value of $\Delta$ R/R either at the start of the measurement, or after a short delay after the sample is placed in the measurement position under exposure to the pump and probe beams. In corresponding embodiments of the invention, no external irradiation source 37 is required.

The temporal characteristics of the increase in the peak-to-peak value of $\Delta$ R/R may be different depending on the spectral intensity characteristics of the external irradiation source.

The external irradiation source may induce photovoltage effects which are desirable, but may also induce photo-voltage effects which are undesirable. In this latter case, the method should be performed such that the external irradiation is not present on the sample at the same time as a photoreflectance spectrum measurement is being made.

The external irradiation source will preferably be a continuous irradiation source, but need not be, and in some embodiments of the invention may be a pulsed or an amplitude modulated or chopped or spatially modulated external irradiation source.

In some embodiments of the invention, the external irradiation source will be such that it is incapable of photo-inducing certain types of dissociation or other chemical reactions, but in other embodiments of the invention, the external irradiation source will be such that it is capable of photo-inducing certain types of dissociation or other chemical reactions. For example, under certain conditions, Si—H bonds can be broken using irradiation with photons of greater than 7 eV, and it may be desirable or undesirable to photo-induce such an effect, depending on whether it increases or decreases the peak-to-peak value of $\Delta$ R/R.

In some embodiments of the invention, where a pump beam source such as a laser is used, the pump laser wavelength may be chosen to be such that it can photo-induce an increase in the photoreflectance peak to peak signal, whereas in other embodiments of the invention, the pump laser wavelength may be chosen to avoid a photo-induced increase in the peak-to-peak value of $\Delta$ R/R due to the pump beam itself.

The photo-induced increase in the peak-to-peak value of $\Delta$ R/R may be different in magnitude and in temporal characteristics for different types of semiconductor samples and structures, and in some cases, a decrease, rather than an increase, may occur. There may be instances where it is desired to suppress a photoreflectance signal in a sample comprising a multiplicity of semiconductors, and such a decrease if selective may be applied to desirable effect in such cases.

The external irradiation source will in preferred embodiments of the invention be a light source providing sufficient intensity of suitable infrared, visible and/or ultraviolet electromagnetic radiation.

The external irradiation source may in some embodiments of the invention be a source of intense ultraviolet radiation, such as a deuterium, Xe arc discharge, Hg arc discharge, or Hg(Xe) arc discharge lamp or lamp system, such as for example a solar spectrum simulator irradiation source.

Other forms of non-ionising or ionising radiation, or an external electric field or voltage induction source, may in some embodiments of the invention be utilised as the external irradiation source, and in some of these embodiments, contact may be made with the sample by a material.

FIG. 4 shows a typical form of the signals and measurement result. The waveform of the modulated reflectance is always periodic, but may be more complex than the single sine wave as shown in FIG. 4, top panel. In one method of use, the lock-in amplifier 35 is used to measure and record the magnitude and phase of the modulated reflectance signal $\Delta$ R in the form of a.c. voltage or current signals from the detector 8 at the frequency of modulation. The magnitude of the constant d.c. voltage or current signal from the detector 8 is also measured and recorded by the analogue-to-digital converter or other meter 34, whose output is read by the controlling computer 36. This constant d.c. voltage or current signal from the detector 8 is the unmodulated reflectance R of the sample at the transmission wavelength $\lambda$ of the monochromator 19, with a very small additional constant luminescence signal, which is negligible by comparison to the size of the reflectance signal.

The result of the measurement is expressed as the dimensionless quantity $\Delta$ R/R. The measurement of $\Delta$ R/R is repeated at a number of wavelengths by programmably adjusting the transmission wavelength of the monochromator

53, to acquire a spectrum of the modulated reflectance Δ R/R of the sample 5. The Δ R/R spectrum may fitted to or otherwise analysed using one of a number of well-known formalisms describing the physical origins of the features of the spectrum, which include formalisms of the Third Derivative Functional Form TDFF referred to in the description of the invention. The E1 transition energy is extracted from these fitting procedures.

In general terms, the system performs as follows:

(a) the irradiation of the sample or part thereof whose photoreflectance spectrum is to be measured, for a period of time, either using an external irradiation light source or else using exposure to the probe beam or the pump beam prior to commencing the measurement, (b) the delivery the probe beam to a sample, its specular reflection from the sample, and the steering of the reflected light beam called the "reflected probe beam" onto the photodetector, (c) periodic illumination of the area of incidence of the probe beam on the sample by means of the pump beam at a modulation frequency F, and with light of a photon energy which in the case of a semiconductor is greater than the bandgap energy of the semiconductor, and in the case of other sample materials which is of sufficient energy to photogenerate charge carriers in the material, (d) detection of the time-invariant reflected probe beam intensity denoted R and any amplitude modulated time-variant component of the reflected probe beam intensity denoted Δ R at the amplitude modulation frequency F of the pump laser beam such that their ratio denoted Δ R/R is known, at a number of different photon energies i.e. wavelengths of the probe beam, (e) analysis of the photoreflectance spectrum Δ R/R as a function of the probe beam photon energy in order to determine the transition energy of one or more of the electronic transitions in the sample which causes the appearance of the photoreflectance lineshape signals in the photoreflectance spectrum. These transition energies may be used to determine strain and/or alloy mole fraction in at least one semiconductor layer in the sample, and (f) analysis of other parameters derived from the analysis of the photoreflectance spectrum Δ R/R as a function of the probe beam photon energy, including amplitude, lineshape broadening energy, and lineshape phase, in order to deduce empirical or analytical information or parameters characteristic of the degree of crystallinity, damage, disorder, or surface quality of the near-surface region or the edge of a semiconductor, which has been exposed to sawing, lapping, grinding, polishing or etching processes.

The probe beam 4 may be delivered to the sample as a monochromatic beam, or as a filtered beam, having a selected range of wavelengths, in order to expose the sample to the useful part of the spectrum.

Both the reflectance R of the probe beam, and the modulation of the reflectance Δ R of the probe beam are measured at a multiplicity of probe beam photon energies i.e. different wavelengths of the probe beam, and may be measured at a multiplicity of locations on the sample and their ratio Δ R/R which is called the photoreflectance is calculated or measured directly at a multiplicity of beam photon energies to give a photoreflectance spectrum. A part of the photoreflectance spectrum, within which the photoreflectance signal varies in magnitude at different probe beam photon energies, may be referred to as being a photoreflectance lineshape or as comprising one or more photoreflectance lineshapes.

The photoreflectance spectrum comprises one or more, often superimposed, photoreflectance lineshape components. These photoreflectance lineshape components are generally found to conform to the formalism of Aspnes known as the third derivative function form TDFF or "low-field" photoreflectance lineshape. This models the case of the photoreflectance effect in which any d.c. electric fields which are in-built in the semiconductor are insufficient to produce practically measurable Franz-Keldysh effects in the photoreflectance spectrum. This formalism of Aspnes is a derivative with respect to photon energy of a Lorenztian lineshape, the index m being selected differently with respect to the dimensionality of the direct interband transition in the Brillouin zone, and the photoreflectance spectrum Δ R/R(E) due to a single photoreflectance lineshape component of this type is represented by the Expression 1

$$\Delta R/R(E) \sim A\, Re[e^{i\theta}(E-E_g+i\Gamma)^{-m}] \quad (1)$$

where:
A is an amplitude factor
θ is a lineshape phase factor
Eg is the transition energy
Γ is a broadening energy parameter
m is a critical point transition dimensionality parameter, generally 2.5 or 3.0

The analysis of a photoreflectance spectrum comprising one or more of these lineshapes consists in the calculation of the theoretical photoreflectance spectrum obtained by the summation of one or more components represented by expressions of type 1, and adjusting parameters within these expressions 1 using a regression fitting programme, for example, that of Levenberg and Marquardt, to minimize the error between the theoretically calculated photoreflectance spectrum and the measured photoreflectance spectrum. The parameters required in Expression 1 for the minimized error are accepted as the material parameters, and specifically in this case, the values of the transition energy Eg for each component can be determined by this fitting procedure. One or more of the parameters in expression 1 may be fixed for one or more of the photoreflectance lineshapes.

In one example, the photoreflectance spectrum of a strained silicon layer on insulator (SSOI) wafer was measured over the spectral range 2.8 eV to 3.7 eV at intervals of 0.002 eV, following irradiation for 10 seconds using a 300 W Xe arc lamp coupled into an 800 micron diameter core optical fibre and collimating the radiation emerging from the optical fibre for use as the external irradiation light source. The peak-to-peak value of the photoreflectance ratio ΔR/R was found to be increased after the irradiation compared to prior to the irradiation, leading to an enhancement of the signal-to-noise ratio of the spectrum, and a consequential improvement of the repeatability of the measurement. This spectrum was fitted to a summation of two low field photoreflectance lineshapes, and was found to have an E1+ transition energy of 3.300 eV, shifted 103 meV from the E1 transition energy of 3.403 eV of an unstrained SOI wafer. Converted to in-plane strain, a value of 0.75% was determined for the in-plane strain of the top strained silicon layer.

The sample may be a semiconductor, a semiconductor crystal structure, or a semiconductor wafer comprising one or more semiconductor devices and structures, and the pump beam is provided by a laser or other light source whose photon energy is at least greater than the fundamental bandgap energy of one of the semiconductors. At least one photoreflectance lineshape is measured which corresponds to a direct interband transition (also referred to as a direct bandgap or direct optical bandgap) in the semiconductor layer which has generated it. This photoreflectance lineshape is analysed to yield the energy of this direct interband transition.

At least two photoreflectance lineshapes may be measured which correspond to at least two direct interband transitions also referred to as a direct bandgap or direct optical bandgap in either the same or different semiconductor layers which have generated them. These photoreflectance lineshapes are analysed to yield the energy of these direct interband transitions.

The method may include the further steps of analysing the energy of one or more of the interband transitions, measured by photoreflectance spectroscopy, to measure the strain in the semiconductor layer to which it is associated. The method may include the further steps of analysing the energy of one or more of the direct interband transitions, measured by photoreflectance spectroscopy, to measure the alloy mole fraction in the semiconductor layer to which it is associated.

One or more phase shifts may be introduced into the modulated reflected probe beam intensity component electrical signal from the photodetector, such that the signal may be measured under several different phase conditions and a phase analysis may be performed. The lock-in amplifier may contain the necessary electronic devices to perform this phase shifting. Phase shifting may be used to maximise the photoreflectance signal as well as minimising or even rejecting background signals. Phase shifting may also be used, with subsequent analysis, to determine the relative phase of two different photoreflectance lineshapes in a photoreflectance spectrum.

The sample may be one of the following semiconductor wafer types: silicon; germanium; silicon-germanium alloy; silicon-germanium-carbon alloy; silicon-germanium alloy whether strained or not on silicon; silicon-germanium-carbon alloy whether strained or not on silicon; dielectric layer on silicon; dielectric layer on germanium; dielectric layer on silicon-germanium alloy; dielectric layer on silicon-germanium-carbon alloy; silicon on insulating layer including silicon oxide layers on silicon; strained silicon on silicon-germanium-carbon alloy on silicon; strained silicon on insulating layer including silicon oxide layers on silicon; strained silicon on silicon-germanium alloy on insulating layer including silicon oxide layers on silicon; silicon-germanium alloy whether strained or not on insulating layer including silicon oxide layers on silicon; germanium whether strained or not on silicon-germanium alloy; germanium whether strained or not on silicon; silicon whether strained or not on germanium whether strained or not.

In many cases the photoreflectance signal is obtained from the top semiconductor layer. In some cases, the semiconductor may have been processed by one or more of sawing, lapping, grinding, polishing or etching processes. In some of these cases, it may be desired to measure on the edge, for example the sawn edge, of the semiconductor.

Measurement of Biaxial Strain in Silicon

The invention finds particular application to the measurement of strain in silicon, and especially anisotropic forms of strain including biaxial strain.

Strain in silicon can be of types other than hydrostatic, and can be deliberately induced by means of crystallographic epitaxial growth and the manipulation of crystal lattice constant parameters. There are good reasons for inducing certain types of directional strain in silicon, which are related to the consequential changes in electronic band structure which result in either or both types of charge carrier in the semiconductor, electrons and/or holes, having enhanced carrier mobility resulting in faster electronic devices for a given device geometry. This is of high industrial importance, and has created a requirement to measure certain types of directional crystallographic strain in various silicon and silicon-germanium alloy semiconductor structures. The most useful types of strain to induce in silicon are biaxial and uniaxial.

Figure 5:
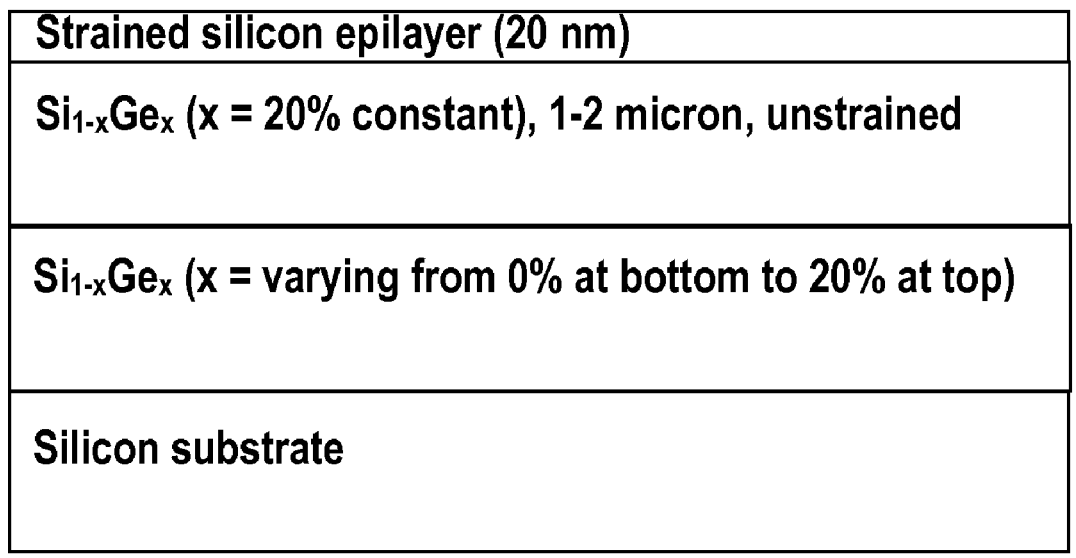
FIG. 5 is a diagram of an epitaxial crystalline structure in which a top silicon layer is biaxially strained.

Biaxial strain in silicon is usually induced by epitaxial growth of a series of crystallographic layers on a silicon substrate, terminating with a thin silicon overlayer which is strained. FIG. 5 shows a typical structure, in which a graded composition layer of Si1-xGex alloy is grown such that the Ge alloy mole fraction x increases upward from 0% at the silicon substrate to some value, typically 20%, at which point the Ge % is maintained constant and a further layer of Si1-xGex alloy is grown at fixed composition. Many such structures are designed such that the fixed composition Si1-xGex alloy layer is fully relaxed unstrained, and adopts a lattice constant which is determined by the Ge alloy mole fraction x, and which is larger than the lattice constant of unstrained silicon. Finally, a thin silicon layer, which it is usually intended to strain, is grown on top of the fixed composition Si1-xGex alloy layer.

Figure 6:
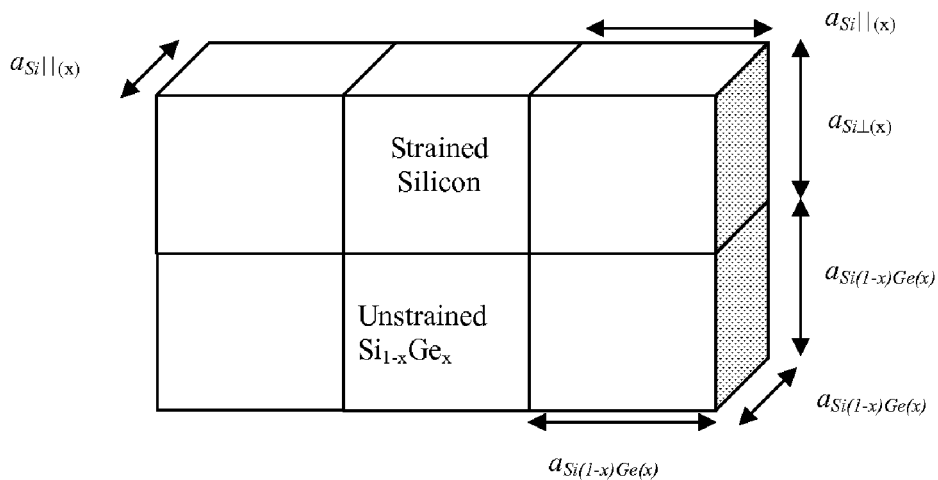
FIG. 6 is a diagrammatic perspective view showing how an epitaxial silicon layer grown pseudomorphically on a silicon-germanium alloy layer is biaxially strained.

FIG. 6 shows in more detail the thin top silicon layer and the fixed composition Si1-xGex alloy layer, and in particular, their lattice constants denoted a in different directions. The lattice constant of the fixed composition Si1-xGex alloy layer is generally the same in all principal directions and is denoted as aSi1-xGex. The top silicon layer is formed pseudomorphically, meaning that its in-plane lattice constant $\alpha_{Si||x}$ is the same as that of the fixed composition $Si_{1-x}Ge_x$ alloy layer layer $\alpha_{Si1-xGex}$. The Bir-Pikus Hamiltonian for a Γ1 type band has the form 2 given by S. Richard, F. Aniel, G. Fishman and N. Cavassilas in J. Appl. Phys. 94 no. 3 (2003) pages 1795-1799 and allows the calculation of the lattice constant of the fixed composition $Si_{1-x}Ge_x$ alloy layer $\alpha_{Si1-xGex}$ from the well-known values of the lattice constants of unstrained bulk silicon $\alpha_{Si}$ and germanium $\alpha_{Ge}$, and a knowledge of the Ge alloy mole fraction x:

$$a(Si_{1-x}Ge_x)=a(Si)+0.200326x(1-x)+[a(Ge)-a(Si)]x^2 \qquad (2)$$

Therefore, the in-plane lattice constant of the strained top silicon layer is known to be larger than in unstrained bulk silicon. Poisson behaviour predicts that the out-of-plane lattice constant of the strained top silicon layer must be smaller than in unstrained bulk silicon, and by a predictable proportion given by the elastic constants $C_{11}$ and $C_{12}$ of the silicon. Thus the top silicon is biaxially strained.

We define the following parameters. $\in_\perp$ is strain along [001] direction perpendicular to growth, and is in-plane strain. The 001 strain tensor elements take the form given by G. L. Bir and G. E. Pikus, "Symmetry and Strain-Induced Effects in Semiconductors" Wiley, New York, 1974

$$\varepsilon_{xx} = \varepsilon_{yy} = \varepsilon_\| = \frac{a(Si_{1-x}Ge_x) - a(Si)}{a(Si)} \qquad (3)$$

$$\varepsilon_{zz} = \varepsilon_\perp = -2\frac{C_{12}}{C_{11}}\varepsilon_\| \qquad (4)$$

$$\varepsilon_{xy} = \varepsilon_{xz} = \varepsilon_{yz} = 0 \qquad (5)$$

where $C_{11}$ and $C_{12}$ are the elastic constants of silicon.

The biaxial strain may be considered as a combination of tensile hydrostatic strain and compressive uniaxial strain along the growth axis the out-of-plane normal axis. These two deformations each have a different effect on the direct optical transition energy E1 which is the quantity measured by the photoreflectance spectroscopy method for this application. The in-plane tensile hydrostatic strain narrows this bandgap, reducing the direct optical transition energy E1. The compressive uniaxial strain along the growth axis causes the valence band to split at the relevant part of the Brillouin zone where the direct optical transition energy E1 is located. The effect of this is to split the transition into two branches, which can be called E1+ and E1−. The E1− branch shifts back to higher energy, and compared to the value of E1 in unstrained silicon, unexpectedly is found to be almost invariant, as a fortuitous result of the behaviour of biaxially strained silicon. By contrast, the E1+ branch is found to exhibit a narrowing which is linearly proportional to the strain in the silicon.

An aspect of measuring biaxial strain in silicon using photoreflectance, is a knowledge of the relationship between the strain tensor elements $\in_\perp$ and $\in_\parallel$ and the direct interband electronic transition (also sometimes called the optical bandgap) energy $E_1$ measured by the photoreflectance spectroscopy method. While in theory, there are in fact a pair of direct interband electronic transitions $E_1$ and $E_1+\Delta_1$, their PR lineshapes overlap closely in unstrained silicon, and in effect they appear as a single direct interband electronic transition. There is also a lower energy transition $E_0$ but its PR signal is extremely weak and difficult to practically measure. This invention focuses on the practical application of the $E_1$ transition and its strain-related splitting, which gives rise to a relatively strong PR signal. The material parameters relating these two quantities are known as deformation potentials, D. D is a tensor quantity, many of whose relevant elements have been determined for silicon by means of destructively making electrical contacts to a silicon single crystal wafer and using electrical modulation to measure D by electro-modulated reflectance. For biaxial strain in silicon, the relevant deformation potential elements are $D_1^{-1}$, the hydrostatic deformation potential whose best known value is −9.8 eV and $D_3^{-3}$, the intraband strain deformation parameter along [001] whose best known value is +4.7 eV. The shifts ΔE in each branch of the split $E_1$ transition energy and their relationship to the in-plane and out-of-plane strain elements may therefore be written in the form 5, or when the deformation potential values are inserted, 7:

$$\Delta E = \sqrt{1/3}D_1^{-1}(\in_\perp + 2\in_\parallel) \pm \sqrt{2/3}D_3^{-3}(\in_\perp - \in_\parallel) \quad (6)$$

$$\Delta E = -3.267(\in_\perp + 2\in_\parallel) \pm 1.567(\in_\perp - \in_\parallel) \quad (7)$$

where the "±" sign is applied as "+" to obtain the shift in the $E_1^+$ branch and as "−" to obtain the shift in the $E_1^-$ branch, from the $E_1$ transition energy of unstrained silicon.

One consequence of the existence of two branches of the $E_1$ transition energy in the case of biaxial strain in silicon, one of which is approximately invariant with biaxial strain, is that a standard reference wafer of unstrained silicon is not required for the measurement of strain. The $E_1$ transition energy is very well known for unstrained silicon, and also, inherent in the photoreflectance spectroscopy measurement is a measure of photoreflectance lineshapes yielding the energies of each of the two branches of the $E_1$ transition energy.

The measurement of strain in biaxially strained silicon by means of photoreflectance spectroscopy therefore involves capturing a photoreflectance spectrum, the fitting the spectrum to one or more superimposed derivative Lorentzian lineshape functions of the type developed by Aspnes in order to determine at least the shift in the $E_1^+$ transition energy branch, from the $E_1$ transition energy of unstrained silicon, and the determination of the in-plane strain tensor element $\in_\parallel$ from the expression (7) above which incorporates the deformation potentials for biaxially strained silicon.

Figure 7:
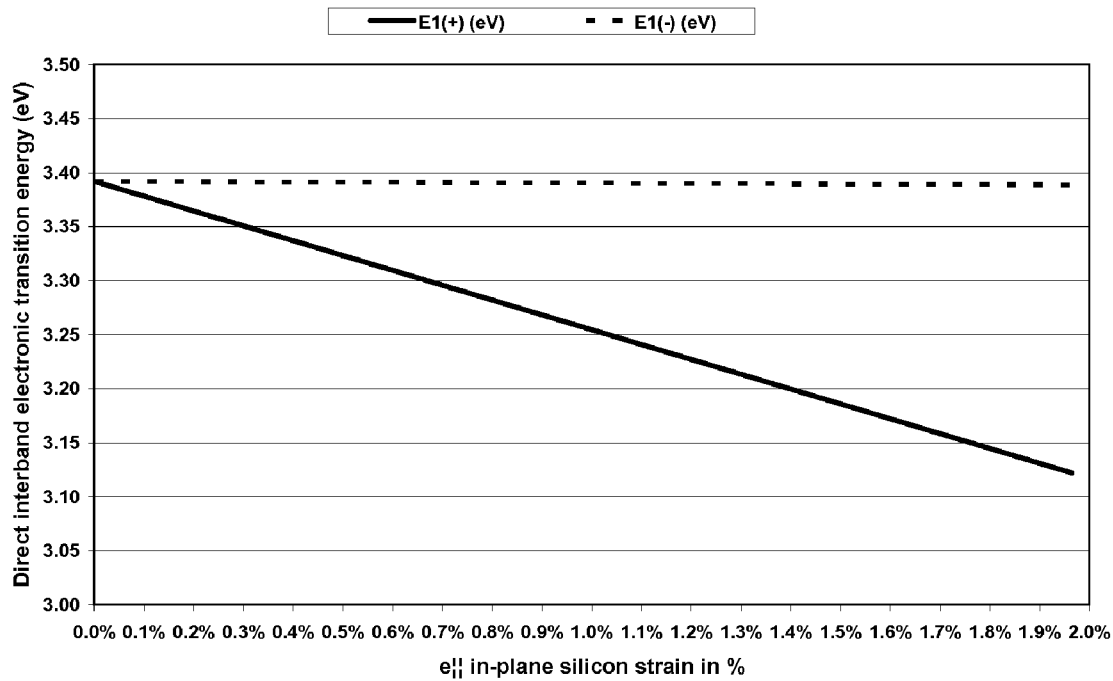
FIGS. 7 to 9 are plots illustrating characteristics for measuring strain in strained silicon.
Figure 8:
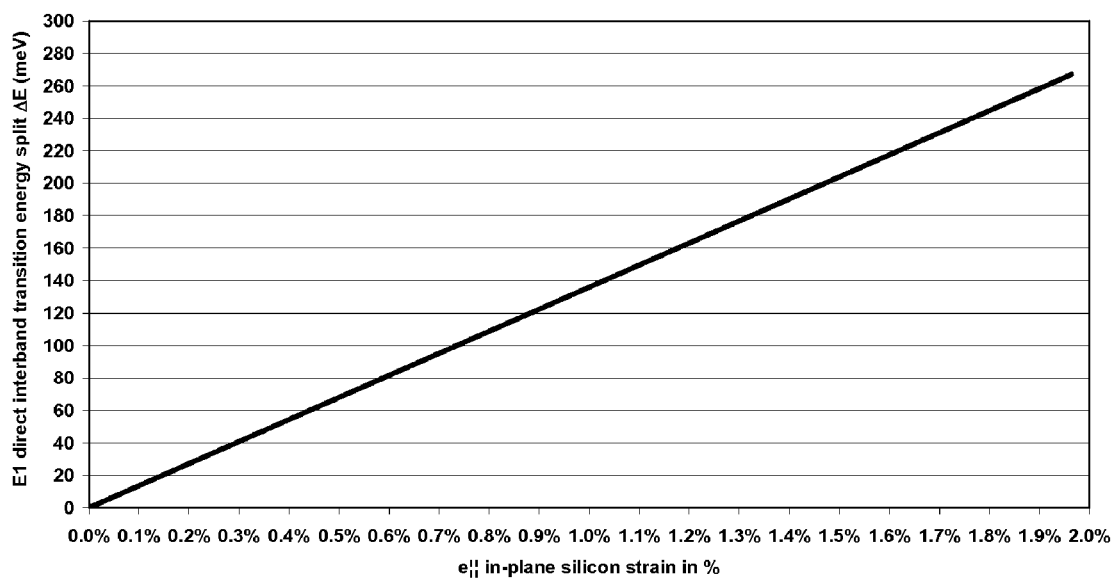

FIG. 7 shows the shift in the direct interband electronic transition energy of the $E_{1+}$ and $E_{1-}$ branches of equation (7), with increasing in-plane tensile strain, for the case of biaxially strained silicon. The $E_{1-}$ transition energy is approximately invariant for these levels of strain, which are representative of the range of strain found in biaxially strained silicon wafers. The $E_{1+}$ transition energy, in contrast, varies strongly in a linear relationship with the in-plane strain. FIG. 8 shows the splitting in the direct interband electronic transition energy $E_1$ of equation (7), with increasing in-plane tensile strain, for the case of biaxially strained silicon.

Measurement of Uniaxial Strain in Silicon

Unixial strain in silicon can be deliberately induced by means of crystallographic epitaxial growth and the manipulation of crystal lattice constant parameters, but is more commonly induced by means of a combination of structural features in a transistor or a test structure of similar geometry and one or more overlayers, typically of silicon nitride or silicon oxynitride. Compressive uniaxial strain in the silicon channel of a transistor or similarly dimensioned test structure can be induced by epitaxial growth of a pair of adjacent regions of $Si_{1-x}Ge_x$ alloy, which has a larger lattice constant and acts to locally compress the silicon in the channel. A silicon nitride film may also be deposited over such a structure, which in the case of a fully functional transistor will include a gate stack and other layers. Tensile or compressive uniaxial strain in the silicon channel of a transistor or similarly dimensioned test structure can be induced by means of the deposition of an overlayer, typically of silicon nitride or silicon oxynitride, and often of variable thickness.

Uniaxial strain has the splitting effect on the direct optical transition energy $E_1$ which causes the valence band to split at the relevant part of the Brillouin zone where the direct optical transition energy $E_1$ is located. The effect of this is to split the transition into two branches, which can be called $E_1^+$ and $E_1^-$. In the case of uniaxial strain, without a hydrostatic component, the first term of expressions 6 and 7 goes to zero, and the splitting is about the unstrained energy of $E_1$, so:

$$\Delta E = \pm \sqrt{2/3}D_3^{-3}(\in_\perp - \in_\parallel) \quad (8)$$

$$\Delta E = \pm 1.567(\in_\perp - \in_\parallel) \quad (9)$$

where the "±" sign is applied as "+" to obtain the shift in the $E_1^+$ branch and as "−" to obtain the shift in the $E_1^-$ branch, from the $E_1$ transition energy of unstrained silicon.

Figure 9:
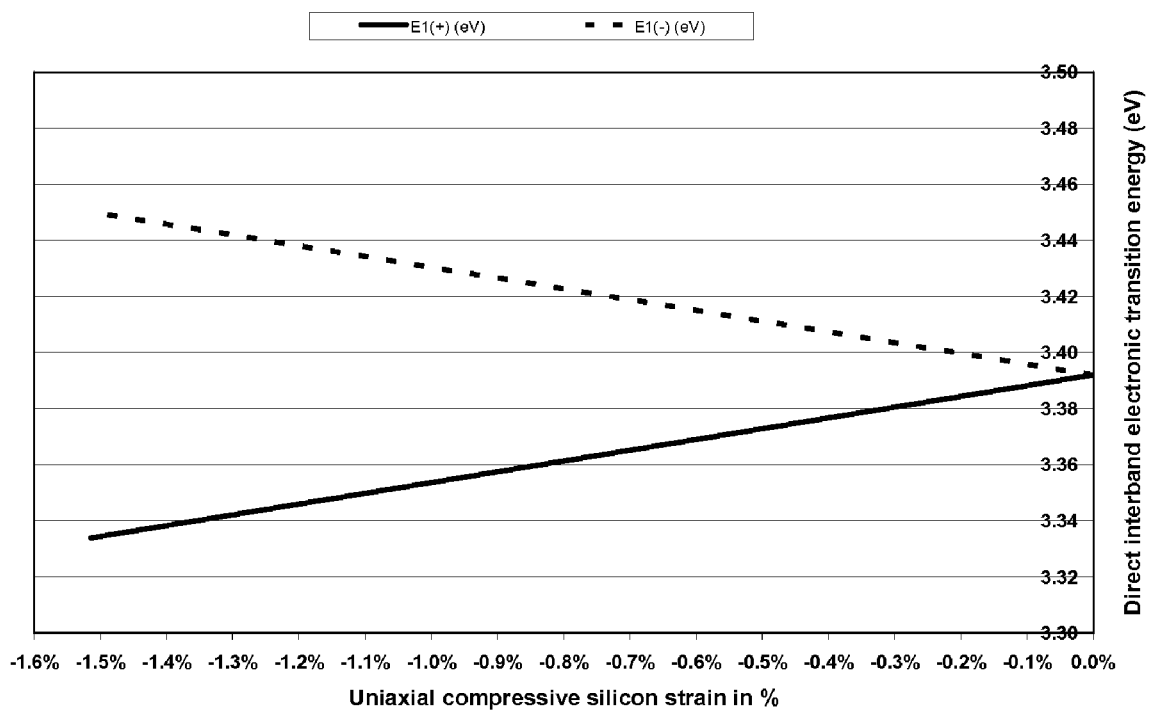

FIG. 9 shows the splitting in the direct interband electronic transition energy $E_1$ of equation (9), with increasing compressive uniaxially strain.

The measurement of strain in uniaxially strained silicon by means of photoreflectance spectroscopy therefore comprises the construction of an apparatus as described in this invention, the making of a photoreflectance spectrum, the fitting of this spectrum to one or more superimposed derivative Lorentzian lineshape functions of the type developed by Aspnes in order to determine at least the shift in the $E_1^+$ transition energy branch, from the $E_1$ transition energy of unstrained silicon, and the determination of the in-plane strain tensor element $\in_\parallel$ from the expression 9 above which incorporates the deformation potential for uniaxially strained silicon.

Measurement of the Alloy Mole Fraction of Silicon-Germanium Alloy

The invention can also be used in a similar manner to determine the alloy mole fraction of silicon-germanium alloys. The known variance of the direct interband transition energies $E_1$ and $E_1+\Delta_1$ in the region of 3.4 eV, valid for x<0.255, is given in (10) and (11)

$$E1(x) = 3.395 - 1.421x - 0.005x2 \quad (10)$$

$$E1 + \Delta 1(x) = 3.424 - 0.848x + 0.214x2 \quad (11)$$

For the case of x=0, these relationships reduce to the direct interband transition energies of bulk silicon. These E1 transitions appear as a single photoreflectance lineshape which gradually splits into a doublet lineshape both components of which are at lower transition energies with increasing germanium content in the silicon-germanium alloy.

Photoreflectance spectroscopy may be applied to measure and analyse the photoreflectance spectrum of a silicon-germanium alloy layer in a similar manner as described in the previous example, but with the conversion of the E1 transition energies to the Ge alloy mole fraction x using the relationships (10) and (11) above.

The foregoing examples illustrate how photoreflectance spectroscopy may be applied to measure strain and alloy mole fraction. Many other models of the behaviour of direct interband transition energies with parameters such as composition and strain of these and other semiconductors may be developed, and similar examples of the method of this invention carried out.

Characterisation of the Surface Quality of a Semiconductor Such as Silicon which has been Exposed to a Surface Treatment Process Surface treatments processes such as etching, sawing, lapping, grinding and polishing can affect the phenomenological appearance of the photoreflectance lineshape, due to changes in one or more of the parameters in equation 1, caused by the surface treatment process.

In one example, a $10^{18}$ cm$^{-3}$ boron-doped silicon wafer was subjected to Argon ion plasma etching at ion acceleration voltages of 150 V and 400 V. Both etch treatments caused the photoreflectance lineshapes to broaden, increase in amplitude, and shift to a different transition energy. However, while the phase of the lineshape changed in both cases, the phase angles were very different, the PR lineshape in the 400 V case being almost inverted from that for the 150 V case. In a similar study, an increase in the oxidation thickness on a similar silicon wafer, from a native oxide to a 20 nm thick oxide, to a 51.2 nm thick oxide, was found to produce both phase and transition energy changes, although with significant changes in the broadening parameter. The characterisation of processes on semiconductor wafers can therefore be performed by observing the empirical trends in selected photoreflectance lineshape parameters.

The invention overcomes a number of difficulties with the prior art in the measurement of strain in semiconductors by other means and significantly advances the methods of modulation spectroscopy by disclosing a new method for modulation spectroscopy measurement of biaxial strain in silicon and alloy mole fraction in silicon-germanium and other alloys, in which the photoreflectance signal to noise ratio is enhanced by means of one or more photo-induced changes to the electrical, electronic or optical properties of the semiconductor, by means of exposure to suitable irradiation from a light source for a time prior to measurement.

An advantageous feature is that it is inherently specific to an ultrathin film of either silicon or silicon-germanium alloy in its information because of its interfacial (surface) electric field modulation, and by means of the strong optical absorption of the low power probe beam, rather than the high power pump laser beam. Moreover, a pump laser wavelength can be employed which is absorbed over a much larger depth than the ultrathin film which is to be measured, because it need only exceed in photon energy the lower indirect bandgap energy of the semiconductor. Thin film specificity is obtained and maintained, because the transition energy measured, the $E_1$ transition or related doublet or splittings of this transition, is the determinant of the spectral position of the onset of optical absorption in these indirect fundamental bandgap semiconductors. Even if these transitions shift to lower energy with alloy mole fraction or strain, the optical absorption onset energy spectrally shifts in the same way, so the method is always strongly thin-film specific. Therefore the method is thin film specific, overcoming the difficulties of x-ray diffractometry and conventional visible Raman spectroscopy, while avoiding the heating problems associated with ultraviolet excited Raman spectroscopy.

The invention therefore provides improved methods of strain and alloy composition measurement in technologically important forms of strained silicon and silicon-germanium alloy. Advantageous aspects which result in the improvements recited above are:

(a) use of an irradiation source, which may be a light source, and which may be an external light source, or the probe beam, or the pump beam, to photo-induce an increase in the peak-to-peak value of the photoreflectance signal $\Delta R/R$ within a spectrum, from silicon or other semiconductors, which can be used to improve repeatability of the measurement and to reduce the spectrum measurement time.

(b) use of a weakly absorbed pump laser beam combined with a strongly absorbed probe light beam in a photoreflectance spectrometer to measure the $E_1$ transition energy and thereby the strain in silicon thin films avoiding heating effects or long measurement times (c) use of the same method in related applications to measure the alloy mole fraction of silicon-germanium and other alloy films The development of a method of strain measurement in silicon and silicon-germanium alloys, especially biaxial and uniaxial strain, based on photoreflectance spectroscopy, which is both sensitive to ultrathin films of semiconductor while avoiding pump laser heating issues, represents an important improvement in this field.

The invention finds general application in the following technical fields, among others:—

- Characterisation of semiconductor surfaces and interfaces
- Characterisation of chemical, ion, electron, or plasma induced damage or modification effects in semiconductor layers and wafers or at their surfaces and interfaces
- Characterisation of semiconductor heterostructures and related devices.
- Characterisation of strain effects in semiconductor layers and wafers
- Measurement of surface and interfacial electric fields in semiconductor layers and wafers in certain types of semiconductor which exhibit Franz-Keldysh effects.
- Measurement of the bandgap energy or interband transition energies of semiconductor layers
- Determination of strain from the bandgap energy or interband transition energies of semiconductor layers
- Measurement of the alloy mole fraction in compound semiconductor layers and wafers The invention finds specific application in the following technical fields, among others:—

- Measurement of the bandgap energy or interband transition energies of semiconductor layers composed of silicon, germanium, or alloys of silicon, germanium and carbon, and including insulating layers, and especially in ultrathin layer of silicon and silicon germanium-alloy where this invention enjoys special advantages over other methods of strain measurement.
- Determination of strain and/or alloy mole fraction from the bandgap energy or interband transition energies of these semiconductor layers, and especially in ultrathin layer of silicon and silicon germanium-alloy where this invention enjoys special advantages over other methods of strain measurement.

Characterisation of process-induced damage to semiconductor surfaces and edges, due to plasma etch processes, lapping, sawing, grinding and polishing of the semiconductor wafer.

Any of the measurements or characterisation applications listed above when performed as a function of the application of an external stress to the sample, such as a mechanical or thermal stress, or the stress due to a deposited thin film or lapping, sawing, grinding or polishing processes.

It will be appreciated that the invention provides an improved method and apparatus for the measurement of semiconductor strain by modulation spectroscopy. The method improves upon the prior art in providing a method of measuring strain in ultra-thin silicon and silicon-germanium alloy layers, which is characterised both by a dominance of the signal by that from the ultra-thin layer which it is desired to measure, and avoiding heating effects due to intense, pump laser radiation being strongly absorbed near the semiconductor surface. The invention also discloses a related method for characterising the damage to a semiconductor surface due to plasma etching.

The invention is not limited to the embodiments described but may be varied in construction and detail. For example, there may be spatial or intensity modulation. In embodiments where the probe beam is monochromated prior to incidence on the sample, there may be an auxiliary monochromator for dispersing the wavelengths of light from one or more light beams within an assembly such that only a narrow range of wavelengths of the light are selected and transmitted, and optical components for shaping said light beam and coupling it to other subsystems. Such an auxiliary monochromator subsystem may be interposed between the output probe beam subsystem and the detector subsystem, and optically coupled to the subsystems, said optical coupling in preferred embodiments of the invention being by means of a suitable optical fibre or optical fibre bundle.

Also, there may be a probe beam normalisation detector subsystem, which may form part of the input probe beam subsystem, for detecting a portion of the light derived from the probe beam, together with coupling optics. The apparatus may comprise a microscopic optical means for reducing the diameter of the incidence spot of the light steered to the sample to the minimum size possible having regard to the limitations introduced by diffraction effects and the aberrations inherent in practical lens systems.

There may be a polarising means for polarising the light steered to the sample, at different angles of polarisation relative to the plane of incidence on the sample. There may be probe beam optical intensity modulation.

The variable angle mechanical system may be used to exploit the dependence between the electro-optic function (i.e. the effective band mass and incidence angle) in order to obtain optimum measurement conditions to obtain the maximum signal from certain types of semiconductor sample. There may be a wafer manipulation subsystem for selecting a semiconductor wafer from one or more cassettes or and placing the semiconductor wafer on the sample mounting subsystem such that a selected point on the wafer is at the point of incidence of the light beam from the input probe beam subsystem.

In some embodiments of the invention, the input probe beam subsystem and the principal monochromator subsystem may be replaced by a light source array subsystem comprising an array of monochromatic light sources of different peak wavelengths, together with wavelength-selective optical filters, and/or optical components for shaping one or more light beams from these sources. Also, the invention may be applied to analysis of non-strained semiconductors. For example, it may be applied to analysis of bandgap or transition energy of a semiconductor such as silicon. Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A method for modulation spectroscopy of a semiconductor sample, the method comprising the steps of:
   irradiating for an irradiation time at least a location on the sample at a radiation intensity and a radiation wavelength sufficient to cause a change in the sample for at least an enhanced measurement time,
   halting the irradiation of the sample at the end of the irradiation time,
   directing an incident probe beam at the location on the sample during the enhanced measurement time to produce a reflected probe beam,
   directing a modulated pump beam at the location on the sample during the enhanced measurement time, thereby causing a modulation of the reflected probe beam,
   receiving the reflected probe beam with a detector that generates as output a direct current signal that is proportional to an intensity of the reflected probe beam and an alternating current signal that is proportional to the modulation of the reflected probe beam, and
   analyzing at least a portion of the output generated during the enhanced measurement time but not during the irradiation time to determine properties of the sample.

2. The method of claim 1, wherein the sample is irradiated during the irradiation time by at least one of the probe beam, the pump beam, and a beam other than either the probe beam or the pump beam.

3. The method of claim 1, wherein the changes are transient.

4. The method of claim 1, wherein the changes are permanent.

5. The method of claim 1, wherein the sample is irradiated with at least one of ultraviolet, infrared, and visible radiation.

* * * * *